United States Patent

Hotter

(10) Patent No.: US 9,364,257 B2
(45) Date of Patent: Jun. 14, 2016

(54) ACCESS ASSEMBLY WITH DUAL ANCHOR AND SEAL CAPABILITIES

(71) Applicant: Covidien LP, Mansfield, MA (US)

(72) Inventor: Joseph Hotter, Middletown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/561,600

(22) Filed: Dec. 5, 2014

(65) Prior Publication Data

US 2015/0087915 A1    Mar. 26, 2015

Related U.S. Application Data

(63) Continuation of application No. 12/944,184, filed on Nov. 11, 2010, now Pat. No. 8,926,508.

(60) Provisional application No. 61/287,396, filed on Dec. 17, 2009.

(51) Int. Cl.
*A61B 1/32* (2006.01)
*A61B 17/34* (2006.01)
*A61B 17/02* (2006.01)
*A61B 17/00* (2006.01)

(52) U.S. Cl.
CPC ......... *A61B 17/3423* (2013.01); *A61B 17/0218* (2013.01); *A61B 17/3421* (2013.01); *A61B 17/3431* (2013.01); *A61B 17/3439* (2013.01); *A61B 17/3462* (2013.01); *A61B 17/3498* (2013.01); *A61B 2017/00942* (2013.01); *A61B 2017/0225* (2013.01); *A61B 2017/3419* (2013.01); *A61B 2017/3441* (2013.01); *A61B 2017/3486* (2013.01)

(58) Field of Classification Search
CPC ........... A61B 17/0218; A61B 17/3423; A61B 17/3421
USPC .......................... 606/192, 213; 600/205–207; 604/101.01–101.05, 103, 917–920
See application file for complete search history.

(56) References Cited

U.S. PATENT DOCUMENTS

| | | | |
|---|---|---|---|
| 3,788,318 A | 1/1974 | Kim et al. | |
| 4,411,655 A | 10/1983 | Schreck | |

(Continued)

FOREIGN PATENT DOCUMENTS

WO    96/36283    11/1996

OTHER PUBLICATIONS

European Search Report for corresponding EP 10 25 2126 application, date of completion is Apr. 18, 2011 (3 pages).

*Primary Examiner* — Ellen C Hammond
*Assistant Examiner* — Stuart S Bray

(57) ABSTRACT

A cannula assembly includes a cannula adapted for insertion within tissue and having a longitudinal passage extending along a longitudinal axis of the cannula for passage of a surgical instrument. An expandable member is mounted to the cannula and longitudinally spaced from a distal end of the cannula. The expandable member is adapted to expand, upon introduction of fluids therein, in a radially outward direction relative to the longitudinal axis whereby the expandable member engages the tissue to facilitate anchoring of the cannula relative to the tissue, and also to expand in a radially inward direction relative to the longitudinal axis and within the longitudinal passage to engage the surgical instrument positioned within the longitudinal passage to facilitate formation of a seal about the surgical instrument.

15 Claims, 4 Drawing Sheets

(56) References Cited

U.S. PATENT DOCUMENTS

| | | | |
|---|---|---|---|
| 5,158,545 A | 10/1992 | Trudell et al. | |
| 5,163,949 A | 11/1992 | Bonutti | |
| 5,183,464 A | 2/1993 | Dubrul et al. | |
| 5,201,756 A | 4/1993 | Horzewski et al. | |
| 5,295,994 A | 3/1994 | Bonutti | |
| 5,318,588 A | 6/1994 | Horzewski et al. | |
| 5,320,611 A | 6/1994 | Bonutti et al. | |
| 5,407,430 A | 4/1995 | Peters | |
| 5,460,170 A | 10/1995 | Hammerslag | |
| 5,505,710 A | 4/1996 | Dorsey, III | |
| 5,514,153 A * | 5/1996 | Bonutti | A61B 17/3439 600/204 |
| 5,573,517 A | 11/1996 | Bonutti et al. | |
| 5,674,240 A | 10/1997 | Bonutti et al. | |
| 5,697,946 A | 12/1997 | Hopper et al. | |
| 5,827,227 A | 10/1998 | DeLago | |
| 5,827,318 A | 10/1998 | Bonutti | |
| 5,860,997 A | 1/1999 | Bonutti | |
| 5,871,474 A | 2/1999 | Hermann et al. | |
| 5,882,345 A | 3/1999 | Yoon | |
| 5,944,691 A | 8/1999 | Querns et al. | |
| 5,954,739 A | 9/1999 | Bonutti | |
| 5,957,902 A | 9/1999 | Teves | |
| 5,961,499 A | 10/1999 | Bonutti et al. | |
| 6,090,072 A | 7/2000 | Kratoska et al. | |
| 6,162,236 A | 12/2000 | Osada | |
| 6,171,299 B1 | 1/2001 | Bonutti | |
| 6,183,443 B1 | 2/2001 | Kratoska et al. | |
| 6,228,068 B1 | 5/2001 | Yoon | |
| 6,270,484 B1 | 8/2001 | Yoon | |
| 6,277,136 B1 | 8/2001 | Bonutti | |
| 6,338,730 B1 | 1/2002 | Bonutti et al. | |
| 6,387,095 B1 | 5/2002 | Kennett et al. | |
| 6,447,489 B1 | 9/2002 | Peterson | |
| 6,613,038 B2 | 9/2003 | Bonutti et al. | |
| 6,702,787 B2 | 3/2004 | Racenet et al. | |
| 6,814,715 B2 | 11/2004 | Bonutti et al. | |
| 6,960,188 B2 | 11/2005 | Jorgensen | |
| 6,972,026 B1 | 12/2005 | Caldwell et al. | |
| 7,311,719 B2 | 12/2007 | Bonutti | |
| D614,297 S | 4/2010 | Criscuolo et al. | |
| 7,744,626 B2 * | 6/2010 | Mollenauer | A61B 17/00234 604/256 |
| 7,942,847 B2 | 5/2011 | Stupecky et al. | |
| 7,942,850 B2 * | 5/2011 | Levit | A61M 25/1002 604/103.07 |
| 8,029,522 B2 * | 10/2011 | Ortiz | A61B 17/3421 606/153 |
| 8,043,362 B2 | 10/2011 | Gong et al. | |
| 8,343,106 B2 * | 1/2013 | Lopez | A61B 17/3421 604/164.04 |
| 8,372,131 B2 * | 2/2013 | Hestad | A61B 17/3431 606/108 |
| RE44,268 E * | 6/2013 | Kambin | A61B 17/1757 604/164.01 |
| 8,636,724 B2 * | 1/2014 | Wiita | A61M 25/0069 604/101.01 |
| 8,808,329 B2 * | 8/2014 | Bonutti | A61B 17/0401 606/232 |
| 8,812,116 B2 * | 8/2014 | Kaula | A61B 5/0488 600/554 |
| 8,814,902 B2 * | 8/2014 | Bonutti | A61B 17/0401 606/232 |
| 8,926,508 B2 * | 1/2015 | Hotter | A61B 17/3421 600/207 |
| 9,089,347 B2 * | 7/2015 | Sankaran | A61B 17/1617 |
| 2001/0012946 A1 | 8/2001 | MacKenzie et al. | |
| 2002/0002360 A1 | 1/2002 | Orth et al. | |
| 2002/0010440 A1 | 1/2002 | Segesser | |
| 2002/0052624 A1 | 5/2002 | Bonutti et al. | |
| 2002/0052625 A1 | 5/2002 | Bonutti et al. | |
| 2003/0014068 A1 | 1/2003 | Bonutti et al. | |
| 2003/0114878 A1 * | 6/2003 | Diederich | A61M 29/02 606/192 |
| 2004/0049222 A1 | 3/2004 | Schaeffer et al. | |
| 2004/0097949 A1 | 5/2004 | Bonutti | |
| 2004/0098016 A1 | 5/2004 | Bonutti | |
| 2004/0098021 A1 | 5/2004 | Laguna | |
| 2004/0106942 A1 | 6/2004 | Taylor et al. | |
| 2004/0127930 A1 | 7/2004 | Bonutti | |
| 2004/0138689 A1 | 7/2004 | Bonutti | |
| 2004/0138702 A1 | 7/2004 | Peartree et al. | |
| 2004/0143285 A1 | 7/2004 | Bonutti | |
| 2004/0172041 A1 | 9/2004 | Gresham et al. | |
| 2004/0193181 A1 | 9/2004 | Bonutti | |
| 2004/0199121 A1 | 10/2004 | Wenchell et al. | |
| 2005/0038408 A1 | 2/2005 | von Segesser | |
| 2005/0113856 A1 | 5/2005 | Epstein et al. | |
| 2005/0124937 A1 | 6/2005 | Kick et al. | |
| 2005/0186244 A1 | 8/2005 | Hunter et al. | |
| 2005/0192608 A1 | 9/2005 | Moreno et al. | |
| 2005/0209627 A1 * | 9/2005 | Kick | A61B 17/22 606/191 |
| 2006/0074374 A1 | 4/2006 | Gresham | |
| 2006/0142795 A1 | 6/2006 | Nguyen et al. | |
| 2006/0212062 A1 | 9/2006 | Farascioni | |
| 2006/0224120 A1 | 10/2006 | Smith et al. | |
| 2007/0250091 A1 | 10/2007 | Makower et al. | |
| 2008/0065140 A1 | 3/2008 | Bonutti | |
| 2009/0221960 A1 * | 9/2009 | Albrecht | A61B 17/3421 604/103.03 |
| 2009/0254064 A1 * | 10/2009 | Boatman | A61M 25/1011 604/509 |
| 2011/0213413 A1 | 9/2011 | Brown et al. | |
| 2012/0179172 A1 * | 7/2012 | Paul, Jr. | A61B 17/0057 606/142 |
| 2012/0238953 A1 * | 9/2012 | Schonholz | A61B 10/02 604/96.01 |
| 2012/0253378 A1 | 10/2012 | Makower et al. | |
| 2013/0023731 A1 * | 1/2013 | Saadat | A61B 1/0008 600/129 |
| 2013/0226146 A1 * | 8/2013 | Tekulve | A61M 25/104 604/509 |
| 2013/0345628 A1 * | 12/2013 | Berger | A61M 25/003 604/101.05 |
| 2015/0005743 A1 * | 1/2015 | McCullough | A61M 25/1011 604/509 |
| 2015/0038767 A1 * | 2/2015 | Isham | A61M 25/1002 600/1 |
| 2015/0142046 A1 * | 5/2015 | Andersen | A61M 25/10 606/196 |

* cited by examiner

ACCESS ASSEMBLY WITH DUAL ANCHOR AND SEAL CAPABILITIES

CROSS-REFERENCE TO RELATED APPLICATIONS

This application is a continuation of U.S. patent application Ser. No. 12/944,184 filed Nov. 11, 2010, now U.S. Pat. No. 8,926,508, which claims benefit of U.S. Provisional Application No. 61/287,396 filed Dec. 17, 2009, and the disclosures of each of the above-identified applications are hereby incorporated by reference in their entirety.

BACKGROUND

1. Technical Field

The present disclosure relates to a cannula for use in a surgical procedure, and more particularly, relates to an anchoring cannula adapted to establish a fixed sealed relation within an incision and provide a seal against an inserted instrument.

2. Description of Related Art

During laparoscopic procedures, cannulas are utilized to provide an access port for surgical instruments and possibly a conduit for introducing insufflation gases (e.g., $CO_2$) into the body cavity. Typically, a sharp trocar is positioned within the cannula and utilized to puncture or pierce the tissue or abdominal wall and removed once the cannula is in place. In some instances, an anchoring structure may be provided with the cannula.

During the insertion and extraction of laparoscopic instruments, insufflation gases may escape through and around the cannula, which, in turn, may cause the body cavity to deflate. In order to impede and/or prevent insufflation gases from migrating through and around the cannula, cannulas may include seal devices that form a seal around the laparoscopic instrument.

SUMMARY OF THE DISCLOSURE

Accordingly, the present disclosure relates to a cannula assembly including a cannula adapted for insertion within tissue and having a longitudinal passage extending along a longitudinal axis of the cannula for passage of a surgical instrument. An expandable member is mounted to the cannula and may be longitudinally spaced from a distal end of the cannula. The expandable member is adapted to expand, upon introduction of fluids therein, in a radially outward direction relative to the longitudinal axis whereby the expandable member engages the tissue to facilitate anchoring of the cannula relative to the tissue, and also to expand in a radially inward direction relative to the longitudinal axis and within the longitudinal passage to engage the surgical instrument positioned within the longitudinal passage to facilitate formation of a seal about the surgical instrument.

The expandable member may include an instrument engaging segment and a tissue engaging segment. The instrument engaging segment and tissue engaging segment may define respective internal chambers. The internal chambers may be in fluid communication. The cannula may include a fluid conduit in fluid communication with the instrument engaging segment and the tissue engaging segment.

The cannula may include first and second fluid conduits in fluid communication with respective internal chambers of the instrument engaging segment and the tissue engaging segment. The internal chamber of the instrument engaging segment may be isolated relative to the internal chamber of the tissue engaging segment. At least one of the instrument engaging segment and the tissue engaging segment may include a bellows structure. The instrument engaging segment may include a lubricious coating. The lubricious coating may be selected from the group consisting of a hydrophilic material, a biocompatible powder, polytetrafluoroethylene.

The cannula may include a zero closure valve adapted to substantially close the longitudinal passage in the absence of a surgical instrument. In the alternative, the instrument engaging segment may expand to substantially close the longitudinally passageway.

BRIEF DESCRIPTION OF THE DRAWING

Various embodiments are disclosed herein with reference to the drawings wherein.

DETAILED DESCRIPTION

Figure 1:
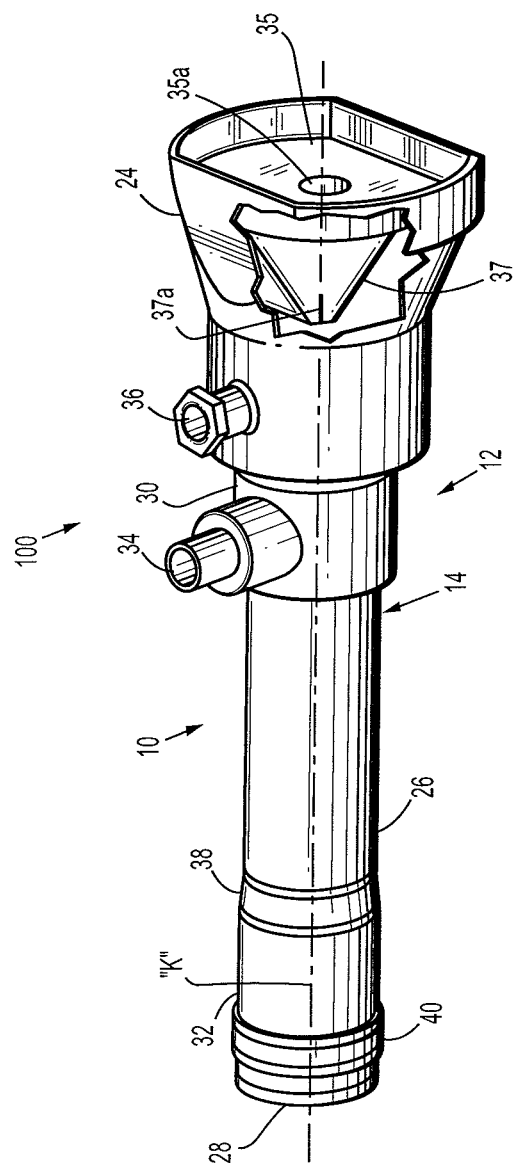
FIG. 1 is a perspective view with portions cut-away of a cannula assembly illustrating an anchor seal in a non-expanded state in accordance with the present disclosure.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions which follow, the term "trailing" or "proximal", as is traditional, will refer to the end of the cannula assembly 100 which is closer to the user, while the term "leading" or "distal" will refer to the end of the cannula assembly 100 which is further from the user.

One type of cannula assembly that may employed with the present disclosure may be of the type as disclosed in commonly owned U.S. Patent Publication No. 2004/0138702, entitled BALLOON CANNULA WITH OVER-CENTER CLAMP, filed on May 31, 2002, the contents of which are hereby incorporated in their entirety by reference.

Figure 2:
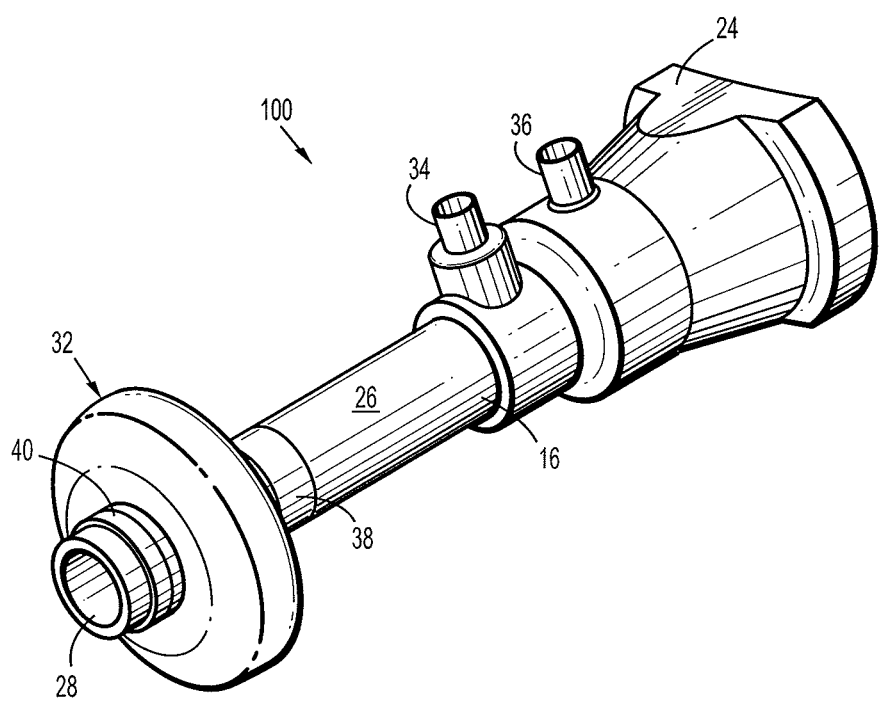
FIG. 2 is a perspective view of the cannula assembly illustrating the anchor seal in an expanded state in accordance with the present disclosure.
Figure 3:
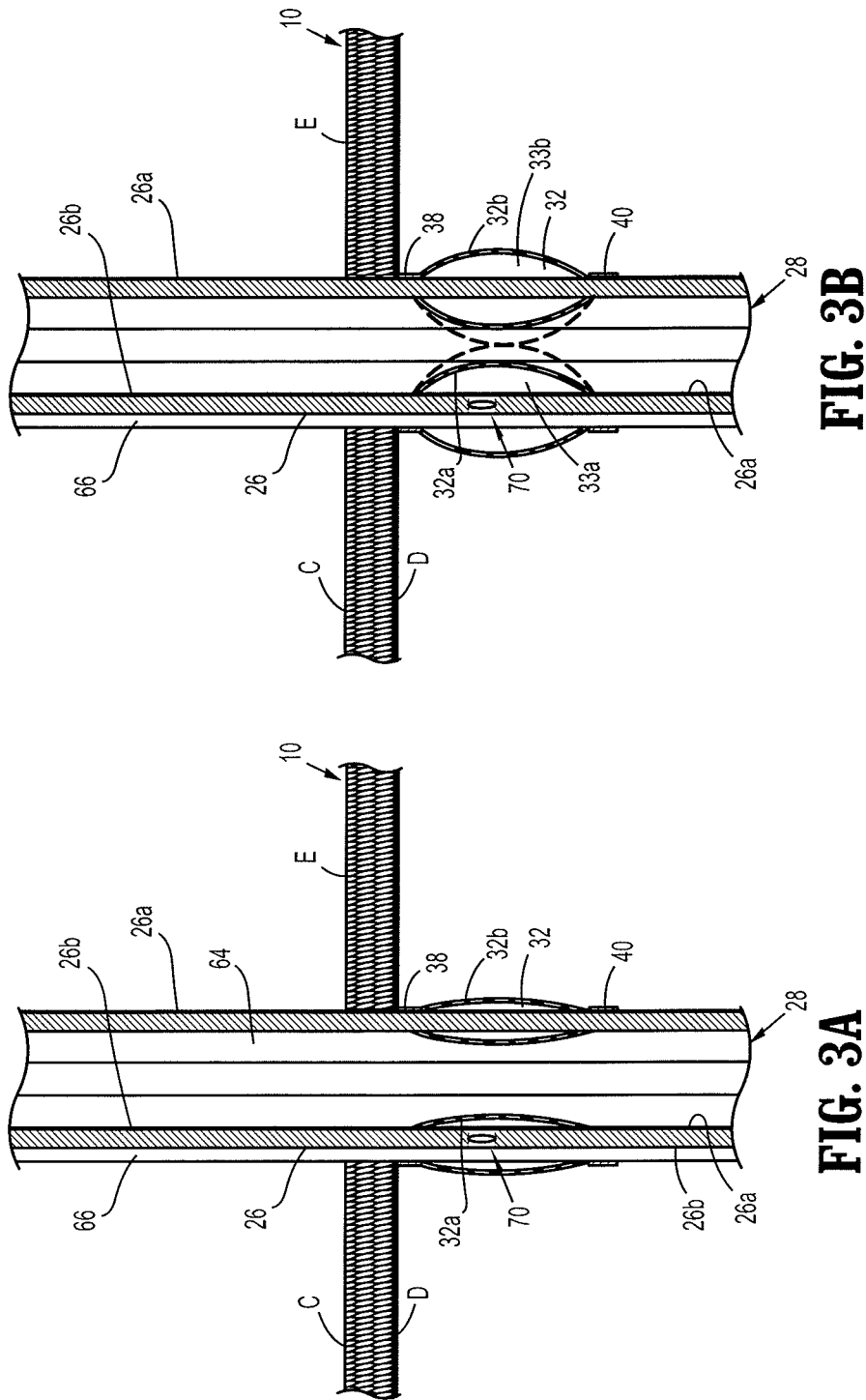
FIG. 3A is a cross-sectional view of the cannula assembly illustrating the anchor seal in a non-expanded state in accordance with the present disclosure.
FIG. 3B is a cross-sectional view of the cannula assembly illustrating the anchor seal in an expanded state in accordance with the present disclosure.

Referring now to FIGS. 1 and 2, cannula assembly 100 is shown. Cannula assembly 100 generally includes housing 24 and cannula shaft 26 extending distally from the housing 24. Housing 24 is dimensioned for engagement by the user. Housing 24 may include an instrument seal 35 and/or a zero closure valve 37. Instrument seal 35 may be adapted to establish a substantial sealed relation about a surgical instrument. In one embodiment, instrument seal 35 defines a slit, aperture or passage 35a for receiving the instrument in sealed relation therewith. Zero closure valve 37 may be a duckbill valve, trumpet valve or the like having a passage 37a adapted to close in the absence of the surgical instrument and/or in response to presence of insufflation gases. A suitable instrument seal and zero closure valve is disclosed in commonly assigned U.S. Pat. No. 6,702,787 to Racenet, the entire contents of this disclosure being hereby incorporated by reference herein.

Cannula shaft 26 has a generally tubular shape, and defines a longitudinal axis "k". Cannula 100 may also include an insufflation port 36 which is in fluid communication with the interior of shaft 26 so as to provide insufflation fluid into the body. In addition, cannula 100 may include a fluid port 34. Fluid port 34 may be configured to receive a syringe containing inflation fluid, such as, for example, saline, so as to inflate an anchor seal 32.

With continued reference to FIGS. 1-3B, cannula assembly 100 generally defines a through bore 64 extending between distal end 28 and proximal end 30 of cannula shaft 26. Insufflation port 36 is in fluid communication with through bore 64 to provide insufflation fluid to a body cavity. Shaft 26 further defines an inflation lumen or conduit 66 along its length which is in fluid communication with inflation port 34 and one or more apertures 70 in fluid communication with an interior of anchor member 32. Conduit 66 may be a channel formed in the wall of cannula shaft 26 or may be a separate tubing running the length of the cannula shaft 26 either internally or externally.

With continued reference to FIGS. 1-3B, anchor seal 32 will be discussed. Anchor seal 32 may be spaced from distal end 28 of cannula shaft 26. Anchor seal 32 may be an expandable membrane or member 32 mounted to the cannula shaft 26. The expandable member 32 is adapted to expand upon introduction of fluids therein. The fluids may include gases or liquids, and are delivered through inflation port 34 and conduit 66. Expandable member 32 may be configured to expand in a generally radially outward direction relative to the longitudinal axis "k" for engaging tissue and facilitating anchoring of the cannula relative to the tissue, e.g., to a position in which the expandable member 32 is spaced more radially outward relative to an outer surface of the cannula. Additionally, expandable member 32 may be configured to expand in a generally radially inward direction relative to the longitudinal axis and within bore 64, e.g., to a position in which the expandable member 32 is spaced more radially inward relative to an inner surface of the cannula, to facilitate formation of a seal about a surgical instrument positioned within the longitudinal opening of the cannula 24.

In an embodiment, expandable member 32 may be a balloon configured to provide a seal against tissue and about a surgical instrument when balloon 32 is in an expanded state. Expandable member 32 may be defined as having an inner instrument engaging segment 32a and an outer tissue engaging segment 32b. Each segment 32a, 32b may be mounted to cannula shaft 26.

Instrument engaging segment 32a and tissue engaging segment 32b of expandable member 32 may be manufactured from any suitable material known in the available art including but not limited to elastomers, rubber, plastic, polyurethane and the like. In an embodiment, segments 32a and 32b may be elastic. Alternatively, segments 32a and 32b may be non-elastic.

It is envisioned that segments 32a and 32b may each be made from the same material or they may be made from different materials. For example, it may be useful to have instrument engaging segment 32a including a polyurethane film. Instrument engaging segment 32a may be configured in such a manner to conform to the shape of a laparoscopic instrument and/or an object which is brought into contact with it.

Instrument engaging segment 32a may be treated with a material, such as for example: a hydrophilic material which, when wet, becomes slick to facilitate passage of an instrument; a lubricating agent such as biocompatible powder; and polytetrafluoroethylene, such as Teflon®. Alternatively, inner instrument engaging segment 32a may be made from a material that is normally inherently slick. Tissue engaging segment 32b may be made from and/or include any of the aforementioned materials that were described regarding instrument engaging surface 32a.

Tissue engaging segment 32b of expandable member 32 may be secured to an outer surface 26b of shaft 26, by locking rings 38 and 40 located on the proximal and distal sides of balloon 32, respectively. Other securing methods may include glues, adhesives, and the like. Tissue engaging segment 32b may be sleeve-like in configuration with the proximal and distal ends of the sleeve secured to shaft 36.

Instrument engaging segment 32a of expandable member 32 may be secured to an inner surface 26a of shaft 26 in similar fashion as described in regard to tissue engaging surface 32b e.g., locking rings (configured for internal mounting to the inner surface 26a of shaft 26), glues adhesives, and the like. It is contemplated, that tissue engaging segment 32b and instrument engaging segment 32a of expandable member 32 may be secured to shaft 26 by means not herein described. Instrument engaging segment 32b may be sleeve-like in configuration with the proximal and distal ends secured to shaft 36.

Instrument engaging segment 32a and tissue engaging segment 32b of expandable member 32 may be sized and shaped similarly to each other. Conversely, instrument engaging segment 32a and tissue engaging segment 32b may each have a size and shape different from each other. For example, it may be useful to have instrument engaging segment 32a extend along a greater length of shaft 26. Or, it may be useful to have instrument engaging segment 32a, when in an expanded state, exude a shape that will conform to a particular type of surgical instrument.

As described above, located on shaft 26 may be one or more apertures 70. Apertures 70 are in fluid communication with an interior or internal chamber of expandable member 32 and may extend from inner surface 26a to outer surface 26b of shaft 26 providing fluid communication from lumen 66 to each of the internal chambers 33A, 33B of tissue contacting segment 32b and instrument engaging segment 32a.

Instrument engaging segment 32a and tissue engaging segment 32b may be in fluid communication with common insufflation port 34, or each may have their own dedicated insufflation port and/or conduit 66. Instrument engaging segment 32a and tissue engaging segment 32b may define respective internal chambers 33A, 33B which may or may not be in fluid communication.

A brief description of the operation of cannula assembly 100 and operative components associated therewith now follows. The following description is for illustrative purposes only and should not be construed as limiting by any facet.

In use, during a laparoscopic operation, expandable member 32 may be in an initial deflated condition as shown in FIGS. 1 and 3A. A sharp tip trocar (not shown) is inserted through bore 64 and is used to puncture the abdominal wall such that the expandable member 32 is positioned inside or adjacent to the abdominal wall C. The trocar is then removed and a bulb or syringe 78 filled with inflation fluid, such as saline, is inserted in inflation port 34. Fluid is forced through port 34 down lumen 66 and aperture 70 so as to inflate balloon 32 causing tissue engaging segment 32b and instrument engaging segment 32a to begin to expand radially outwardly and inwardly, respectively. After a sufficient amount of inflation fluid has been introduced into expandable member 32, tissue engaging segment 32b, now in a radially expanded state, will press either against the abdominal wall C or within the abdominal tissue, thus preventing loss of gas from the cavity, as shown in FIGS. 2 and 3B. The instrument engaging segment 32a, also in a radially expanded state, will close against itself and against the outer surface of the instrument to form a substantial seal about the instrument thereby preventing loss of gas through the cannula shaft 26 during insertion and manipulation of a laparoscopic instrument (see FIGS. 2 and 3B). It is also envisioned that tissue engaging segment 32b may expand to completely close bore 64 of the cannula shaft 26 in the absence of the instrument as shown in phantom in FIG. 3B.

After laparoscopic operation has been performed, the insufflation gas is withdrawn through insufflation port 36 and syringe 78 may be used to deflate expandable member 32 allowing cannula 100 to be removed from abdominal wall C.

Figure 4:
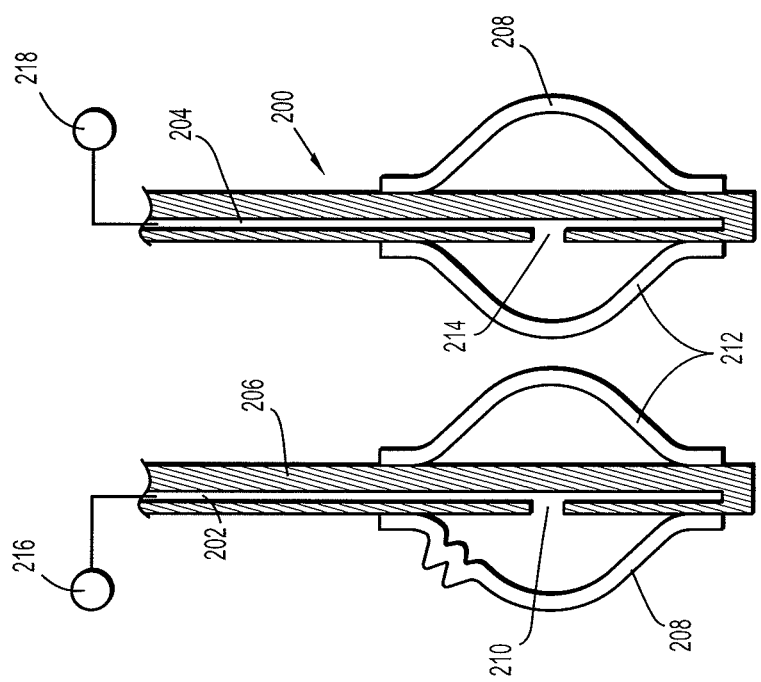
FIG. 4 is a cross-sectional view illustrating another embodiment of the cannula assembly of the present disclosure.

FIG. 4 illustrates an alternate embodiment of the present disclosure. In this embodiment, cannula shaft or sleeve 200 defines first and second longitudinal conduits 202, 204 which are formed in the wall 206 of the shaft sleeve 200. Longitudinal conduit 202 is in fluid communication with tissue engaging segment 208 through aperture 210. Longitudinal conduit 204 is in fluid communication with instrument engaging segment 212 through aperture 214. In one embodiment, a single inflation port may supply the fluids to expand tissue engaging segment 208 and instrument engagement segment 210. In another embodiment as depicted in FIG. 4, first and second inflation ports/sources 216, 218 (shown in schematics) respectively, deliver fluids to first and second longitudinal conduits 202, 204. In a further alternative, tissue engaging segment 212 and/or instrument engaging segment 208 includes a bellows structure 220 adjacent one or both of its ends to facilitate expansion of the tissue engaging segment 212. Bellows structure 220 may facilitate or provide additional expansion capabilities.

From the foregoing and with reference to the various figure drawings, those skilled in the art will appreciate that certain modifications can also be made to the present disclosure without departing from the scope of the same.

It is envisioned that there can be more than one expandable member. For example there can be two, three, four, etc. balloons operatively connected to each other and/or to shaft configured to operate in the same or similar manner as previously described regarding expandable member.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A cannula assembly which comprises:
   a cannula adapted for insertion within tissue, the cannula including a longitudinal passage extending along a longitudinal axis of the cannula for passage of a surgical instrument, and defining proximal and distal ends; and
   an expandable member disposed in mechanical cooperation with the cannula, the expandable member adapted to expand in a radial outward direction relative to the longitudinal axis whereby the expandable member engages the tissue, and in a radial inward direction relative to the longitudinal axis and within the longitudinal passage, wherein at least a portion of the expandable member is disposed radially inward of a portion of the cannula axially aligned therewith, and at least a portion of the expandable member is disposed radially outward of a portion of the cannula axially aligned therewith such that a portion of the cannula physically separates the expandable member into a first internal chamber and a second internal chamber, and wherein at least a portion of the cannula extends distally beyond a distal-most end of the expandable member.

2. The cannula assembly according to claim 1, wherein the first internal chamber includes an instrument engaging segment, and wherein the second internal chamber includes a tissue engaging segment.

3. The cannula assembly according to claim 2, wherein the instrument engaging segment includes a lubricious coating.

4. The cannula assembly according to claim 3, wherein the lubricious coating is selected from the group consisting of a hydrophilic material, a biocompatible powder, and polytetrafluoroethylene.

5. The cannula assembly according to claim 2, wherein at least one of the instrument engaging segment and the tissue engaging segment includes a bellows structure.

6. The cannula assembly according to claim 1, wherein the cannula includes a first fluid conduit in fluid communication with the first internal chamber, and a second fluid conduit in fluid communication with the second internal chamber.

7. The cannula assembly according to claim 6, wherein the first internal chamber is isolated relative to the second internal chamber.

8. The cannula assembly according to claim 1, wherein the cannula includes a zero closure valve adapted to substantially close the longitudinal passage in the absence of a surgical instrument.

9. The cannula assembly according to claim 2, wherein the instrument engaging segment is expandable to close the longitudinal passage in the absence of a surgical instrument.

10. The cannula assembly according to claim 1, wherein at least a portion of the cannula extends proximally beyond a proximal-most end of the expandable member.

11. The cannula assembly according to claim 1, wherein at least a portion of the cannula extends through the expandable member.

12. The cannula assembly according to claim 1, wherein the expandable member is mounted to the cannula.

13. A cannula assembly which comprises:
   a cannula adapted for insertion within tissue, the cannula including a longitudinal passage extending along a longitudinal axis of the cannula for passage of a surgical instrument, and defining proximal and distal ends; and
   an expandable member disposed in mechanical cooperation with the cannula, the expandable member adapted to expand in a radial outward direction relative to the longitudinal axis whereby the expandable member engages the tissue, and in a radial inward direction relative to the longitudinal axis and within the longitudinal passage, wherein at least a portion of the expandable member is disposed radially inward of a portion of the cannula axially aligned therewith, and at least a portion of the expandable member is disposed radially outward of a portion of the cannula axially aligned therewith such that a portion of the cannula physically separates the expandable member into a first internal chamber and a second internal chamber, and wherein at least a portion of the cannula extends proximally beyond a proximal-most end of the expandable member.

14. The cannula assembly according to claim 13, wherein at least a portion of the cannula extends through the expandable member.

15. The cannula assembly according to claim 13, wherein the expandable member is mounted to the cannula.

* * * * *